(12) United States Patent
Baker et al.

(10) Patent No.: US 6,551,975 B1
(45) Date of Patent: Apr. 22, 2003

(54) SANITIZING COMPOSITIONS AND METHODS

(75) Inventors: Keith Homer Baker, Union Township, OH (US); Ulrich Kleinsteuber, Grimbergen (BE); Richard Timothy Hartshorn, Wylam (GB); Massimo Morini, Overijse (BE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/786,933

(22) PCT Filed: Sep. 10, 1999

(86) PCT No.: PCT/US99/21166

§ 371 (c)(1),
(2), (4) Date: Mar. 30, 2001

(87) PCT Pub. No.: WO00/15750

PCT Pub. Date: Mar. 23, 2000

(30) Foreign Application Priority Data

Sep. 15, 1998 (GB) .............................................. 9819979

(51) Int. Cl.$^7$ ............................. C11D 3/395; A61F 2/00
(52) U.S. Cl. ....................... 510/310; 510/312; 510/372; 424/404
(58) Field of Search ................................ 510/367, 310, 510/312, 313, 319, 372, 382, 383, 518; 424/404, 405

(56) References Cited

U.S. PATENT DOCUMENTS

| | | |
|---|---|---|
| 5,021,182 A | 6/1991 | Jentsch |
| 6,287,585 B1 * | 9/2001 | Johansen .................... 424/405 |

FOREIGN PATENT DOCUMENTS

| | | |
|---|---|---|
| WO | WO 93/01716 A1 | 2/1993 |
| WO | WO 94/18297 A1 | 8/1994 |
| WO | WO 97/25106 A1 | 7/1997 |
| WO | WO 98/35005 A1 | 8/1998 |
| WO | WO 99/13037 A1 | 3/1999 |

* cited by examiner

*Primary Examiner*—Mark Kopec
*Assistant Examiner*—John M Petruncio
(74) *Attorney, Agent, or Firm*—James F. McBride; Richard S. Echler, Sr.; Kim W. Zerby

(57) ABSTRACT

A hydrophobic bleaching agent comprising a peroxyacid having a carbon chain of at least 9 carbon atoms is used for the reduction of the activity of micro-organisms that have a cell wall containing high levels of peptidoglycan. Such micro-organisms include yeast and gram positive bacteria.

16 Claims, No Drawings

SANITIZING COMPOSITIONS AND METHODS

CROSS REFERENCE TO RELATED APPLICATIONS

This application claims the benefit of PCT International Application Serial No. PCT/US99/21166, filed Sep. 10, 1999, which in turn claims priority to GB 9819979.7, filed Sep. 15, 1998.

TECHNICAL FIELD

This invention provides methods for improved sanitisation and the use of specific sanitising compositions.

BACKGROUND TO THE INVENTION

Traditionally, hard-surface cleaners contain bleach as cleaning agent and as disinfectant. In particular, they contain high levels of chlorine bleach to achieve the required cleaning and disinfecting properties.

Research has shown that hydrogen peroxide bleach in laundry and dish washing detergents also has a disinfecting action, see for example M Blaser et al. in: *The journal of infectious diseases,* vol 149, no.1,1984.

More recently, detergent manufacturers have become interested in the disinfecting properties of these detergents. Various disclosures describe bleach systems which provide both cleaning and disinfecting during the laundering, for example DE 19616782, DE19605688, DE 19536082, WO9418297. Not all bleach systems which have disinfecting properties are suitable for detergents: they are not always compatible with other detergent ingredients, such as enzymes, or the levels of bleach required to obtain disinfecting are too high and may damage the fabrics.

The inventors now have found that most bleach systems known in the art, including TAED, percarbonate and perborate bleaches, effectively kill gram negative bacteria, but not effectively other micro-organisms, in particular, gram all positive bacteria. Also, it has been found that the antibacterial activity of for example TAED is dependent on the pH, resulting in a strong reduction of anti- bacterial activity on gram positive bacteria at a alkaline pH, such as for example during washing conditions.

Many soils, including body soil, mainly contain micro-organisms other than gram negative bacteria, in particular, gram positive bacteria. The inventors have found that detergents containing for example TAED and a peroxygen source do thus not effectively sanitise these types of soils, in particular at low temperatures as normally used by consumers during laundering, dish washing or other cleaning methods.

They have now found that specific hydrophobic bleaching agent effectively inactivate micro-organisms including gram positive bacteria, such as *Enterococcus hirae* and *Staphyloccocus aureus* bacteria. Thus, when these specific hydrophobic bleaching agents are used in detergents, not only excellent stain removal of bleachable stains and soils is achieved but also sanitisation.

It is believed that the specific hydrophobic bleaching agent have an improved surface activity for the peptidoglycan in the cell walls of, for example, yeast and gram positive bacteria compared to hydrophilic bleaching agents. It is believed that these specific hydrophobic agents thus penetrate and disrupt these cell walls more effectively than other hydrophilic bleaching agents.

Since the specific hydrophobic bleaching agent is found to be very effective, a further benefit can be that reduced levels of bleach can be employed.

Further improved sanitisation can be achieved when both hydrophilic and hydrophobic bleaching agents are employed, resulting in effective inactivation of both gram positive bacteria and gram negative bacteria.

SUMMARY OF THE INVENTION

The invention provides the use of a hydrophobic bleaching agent comprising a peroxyacid having a carbon chain of at least 9 carbon atoms for the reduction of the activity of micro-organism which have a cell wall which contain a high level of peptidoglycan.

When used herein, 'high levels of peptidoglycan' means that the micro-organisms have high levels of peptidoglycan, compared to gram negative bacteria. The cell walls preferably comprise a layer which predominantly comprises peptidoglycan They include yeast and in particular, gram positive bacteria.

When used herein, 'reduction of the activity of the micro-organisms' includes a reduction of the activity as defined in the CEN method prEN1276, 1993, (Comité Européen de Normalisation) and CEN method prEN 1650. The reduction therein is preferably represented by a reduction of micro-organisms, preferably at least of $10^5$, more preferably at least $10^6$ or even more for actaria, or at least $10^4$ or even at least $10^5$ for yeast.

The reduction of the activity of the micro-organisms when used herein includes the reduction of any of the processes conducted by the micro-organisms which have a cell wall including high levels of peptidoglycan, compared to gram negative bacteria., including secretion of products but preferably the growth of the micro-organisms.

The invention also provides a method for reduction of the activity of micro-organisms, or preferably gram positive bacteria comprising the steps of contacting the micro-organism with an aqueous liquor comprising a hydrophobic bleaching agent comprising a peroxyacid having a carbon chain of at least 9 carbon atoms at a level of at least 100 ppm in the liquor, per $10^6$ micro-organisms.

DETAILED DESCRIPTION OF THE INVENTION

Method and Use

The specific hydrophobic bleaching agents herein are used to reduce the activity of specific micro-organisms which have high levels of peptidoglycan in the cell walls, including yeast and gram positive bacteria. In particular, this is done during a sanitisation process or a cleaning process. Hereby, the bleaching agent can be contacted with the specific micro-organisms in solid form, but preferably the bleaching agent is present in a liquor in contact with the micro-organisms.

The specific micro-organisms gram positive bacteria can be present on the surfaces or fabrics to be cleaned and sanitised, for example on the fabrics to be cleaned in a dish washing process or laundry process. The gram positive bacteria can also be present in the liquor used for the cleaning or sanitisation process or in the equipment used in the process, such as the washing machine.

The micro-organisms having cell walls comprising relatively high levels of peptidoglycan, in particular the gram positive bacteria, can be present in soils present on these fabrics or surfaces, in particular in body soils.

The amount of hydrophobic bleaching agent required to obtain effective reduction of the activity of the specific micro-organisms, such as, yeast and gram positive bacteria depends on various factors, such as the amount of micro-organisms present, the conditions of the sanitisation or cleaning process, including the other compounds present, the temperature.

It should be noted that the present hydrophobic bleaching agent may also reduce the activity of micro-organisms which do not comprise high levels of peptidoglycan in their cell walls to a lesser extent, or less efficiently, e.g. gram negative bacteria.

In the method of the invention, the liquor used preferably comprises at least 100 ppm of the hydrophobic peroxyacid per $10^6$ micro-organisms, more preferably at least 200 ppm or even 250 ppm.

The reduction of the activity of the specific micro-organisms, having a peptidoglycan-containing cell walls can be determined by the Petrocci and Clarke method, as described in JOAC 1981, but is preferably determined for the purpose of this invention by the CEN method prEN1276, 1993 for bacteria and CEN method prEN1650 for yeast.

Such a CEN method involves, for example, the preparation of gram positive bacterial inocula conform the DEN method, pages 7 and further, preparation of a solution comprising the hydrophobic bleaching agent at a level of about 250 ppm. conducting the test following the CEN method, incubation TSA plates for 24 hours at 36° C.; and subsequently counting of the bacteria colonies on the plates.

This is compared with the results of the reference and the reduction of bacteria growth is calculated, for the defined contacting time.

Micro-Organisms

The specific micro-organisms herein comprise a cell wall which contain cell walls with high levels of peptidoglycan. In particular, useful herein are yeast and most preferably gram positive bacteria.

The gram positive bacteria are typically present in soils on the fabric, in particular body soils. Typical gram positive bacteria are Enterococcus hirae and *Staphyloccocus aureus*.

Hydrophobic Bleaching Agent

The hydrophobic bleaching agent herein comprises a peroxyacid having a carbon chain of at least 9 carbon atoms. The agent can be a preformed peroxyacid or it can be a compound which provides such a hydrophobic peroxyacid by a chemical reaction, such as the bleach precursors described herein. Also mixtures of these precursor and preformed hydrophobic peroxyacid can be used.

Preferably the hydrophobic bleaching agent comprises a hydrogen peroxide source and a hydrophobic peroxyacid bleach precursor. The production of the hydrophobic peroxyacid occurs by an in situ reaction of the precursor with a source of hydrogen peroxide source. Preferred sources of hydrogen peroxide include inorganic perhydrate bleaches, described hereinafter.

The hydrophobic peroxyacid contains at least 9 carbon atoms, most preferably at least 11 carbon atoms. In a preferred aspect the peroxyacid has an alkyl chain, containing at least 8 or 9 or even at least 10 carbon atoms. Preferably, the peroxy acid but in particular the peroxy acid precursor comprises a N-acyl group.

Preferably, the hydrophobic peroxyacid bleaching agent in a solution is used to reduce the activity of gram positive bacteria, in particular in dish washing or laundry process such that the solution comprises at least 100 ppm of the peroxyacid or peroxyacid precursor per $10^6$ bacteria.

The precursors have a structure

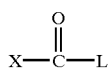

hereinafter L is a leaving group which must be sufficiently reactive for the perhydrolysis reaction to occur within the optimum time frame (e.g., a wash cycle). However, if L is too reactive, this activator will be difficult to stabilize for use in a bleaching composition.

The L groups are preferably selected from the group consisting of:

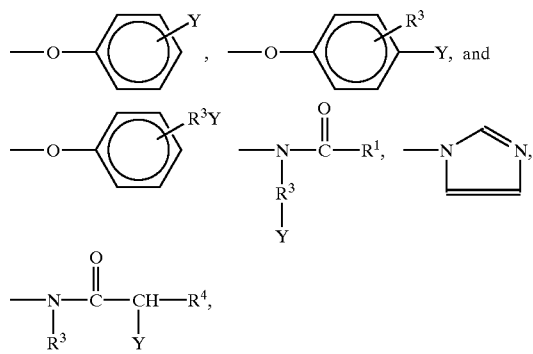

also suitable as L group may be

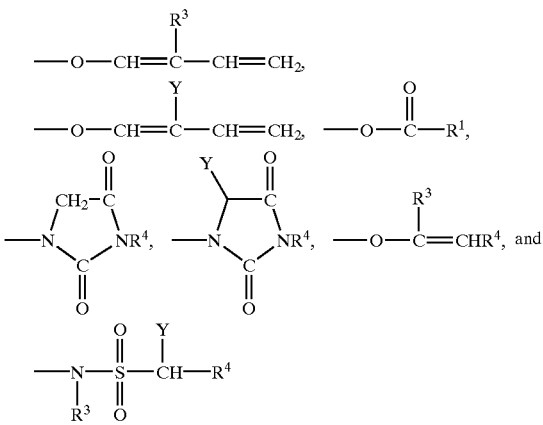

and mixtures thereof, wherein $R^1$ is an alkyl, aryl, or alkaryl group containing from 1 to 14 carbon atoms, $R^3$ is an alkyl chain containing from 1 to 8 carbon atoms, $R^4$ is H or $R^3$, and Y is H or a solubilizing group. Any of $R^1$, $R^3$ and $R^4$ may be substituted by essentially any functional group including, for example alkyl, hydroxy, alkoxy, halogen, amine, nitrosyl, amide and ammonium or alkyl ammmonium groups The preferred solubilizing groups are $—SO_3^-M^+$, $—CO_2^-M^+$, $SO_4^-M^+$, $—N^+(R^3)_4X^-$ and $O{\leftarrow}N(R^3)_3$ and most preferably $—SO_3^-M^+$ and $—CO_2^-M^{30}$ wherein $R^3$ is an alkyl chain containing from 1 to 4 carbon atoms, M is a cation which provides solubility to the bleach activator and X is an anion which provides solubility to the bleach activator. Preferably, M is an alkali metal, ammonium or substituted ammonium cation, with sodium and potassium being most preferred, and X is a halide, hydroxide, methylsulfate or acetate anion.

Suitable hydrophobic peroxyacid bleach precursors herein typically contain one or more N-acyl groups, which precursors can be selected from a wide range of classes. Suitable classes include imides, lactams and acylated derivatives of imidazoles. Suitable N-acylated precursor compounds of the lactam class disclosed generally in GB-A-955735. Preferred materials of this class comprise the caprolactams.

Highly preferred peroxyacid precursors are amide substituted alkyl peroxyacid precursor compounds, including those of the following general formulae:

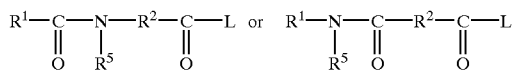

wherein $R^1$ is an aryl or alkaryl group with from about 1 to about 14 carbon atoms, $R^2$ is an alkylene, arylene, and alkarylene group containing from about 1 to 14 carbon atoms, and $R^5$ is H or an alkyl, aryl, or alkaryl group containing 1 to 10 carbon atoms and L can be essentially any leaving group. $R^1$ preferably contains from about 6 to 12 carbon atoms. $R^2$ preferably contains from about 4 to 8 carbon atoms. $R^1$ may be straight chain or branched alkyl, substituted aryl or alkylaryl containing branching, substitution, or both and may be sourced from either synthetic sources or natural sources including for example, tallow fat. Analogous structural variations are permissible for $R^2$. $R^2$ can include alkyl, aryl, wherein said $R^2$ may also contain halogen, nitrogen, sulphur and other typical substituent groups or organic compounds. $R^5$ is preferably H or methyl. $R^1$ and $R^5$ should not contain more than 18 carbon atoms total. Amide substituted bleach activator compounds of this type are described in EP-A-0170386.

Preferred examples of bleach precursors of this type include amide substituted peroxyacid precursor compounds selected from (6-octanamido-caproyl)oxybenzenesulfonate, (6-decanamido-caproyl) oxybenzene-sulfonate, and the highly preferred (6-nonanamidocaproyl)oxy benzene sulfonate, and mixtures thereof as described in EP-A-0170386.

A preferred class of hydrophobic organic :peroxyacid compounds are the amide substituted compounds of the following general formulae:

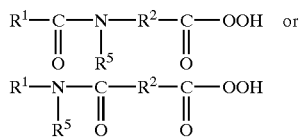

wherein $R^1$ is an aryl or alkaryl group with from about 1 to about 14 carbon atoms, $R^2$ is an alkylene, arylene, and alkarylene group containing from about 1 to 14 carbon atoms, and $R^5$ is H or an alkyl, aryl, or alkaryl group containing 1 to 10 carbon atoms, provided that at least 9 carbon atoms are present. $R^1$ preferably contains from about 6 to 12 carbon atoms, preferably 9 to 12. $R^2$ preferably contains from about 4 to 8 carbon atoms. $R^1$ may be straight chain or branched alkyl, substituted aryl or alkylaryl containing branching, substitution, or both and may be sourced from either synthetic sources or natural sources including for example, tallow fat. Analogous structural variations are permissible for $R^2$. $R^2$ can include alkyl, aryl, wherein said $R^2$ may also contain halogen, nitrogen, sulphur and other typical substituent groups or organic compounds. $R^5$ is preferably H or methyl. $R^1$ and $R^5$ should not contain more than 18 carbon atoms total. Amide substituted bleach activator compounds of this type are described in EP-A-

0170386. Suitable examples, of this class of agents include (6-octylamino)-6-oxo-caproic acid, (6-nonylamino)-6-oxo-caproic acid, (6-decylamino)-6-oxo-caproic acid, magnesium monoperoxyphthalate hexahydrate, the magnesium salt of metachloro perbenzoic acid, 4-nonylamino-4-oxoperoxybutyric acid and diperoxydodecanedioic acid. Such bleaching agents are disclosed in U.S. Pat. Nos. 4,483,781, 4,634,551, EP 0,133,354, U.S. Pat. No. 4,412,934 and EP 0,170,386. A preferred hydrophobic preformed peroxyacid bleach compound for the purpose of the invention is monononylamido peroxycarboxylic acid.

Other suitable organic peroxyacids include diamino peroxyacids, which are disclosed in WO 95/03275, with the following general formula:

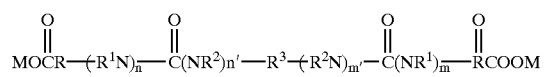

wherein:
R is selected from the group consisting of $C_1$–$C_{12}$ alkylene, $C_5$–$C_{12}$ cycloalkylene, $C_6$–$C_{12}$ arylene and radical combinations thereof;

$R^1$ and $R^2$ are independently selected from the group consisting of H, $C_1$–$C_{16}$ alkyl and $C_6$–$C_{12}$ aryl radicals and a radical that can form a $C_3$–$C_{12}$ ring together with $R^3$ and both nitrogens; $R^3$ is selected from the group consisting of $C_1$–$C_{12}$ alkylene, $C_5$–$C_{12}$ cycloalkylene and $C_6$–$C_{12}$ arylene radicals; n and n' each are an integer chosen such that the sum thereof is 1; m and m' each are an integer chosen such that the sum thereof is 1;

and M is selected from the group consisting of H, alkali metal, alkaline earth metal, ammonium, alkanolammonium cations and radicals and combinations thereof; and provided that the peroxyacid comprises at least 9 carbon atoms;

Other suitable organic peroxyacids are include the amido peroxyacids which are disclosed in WO 95/16673, with the following general structure:

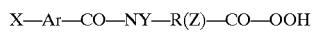

in which X represents hydrogen or a compatible substituent, Ar is an aryl group, R represents $(CH_2)_n$ in which n=2 or 3, and Y and Z each represent independently a substituent selected from hydrogen or an alkyl or aryl or alkaryl group or an aryl group substituted by a compatible substituent provided that at least one of Y and Z is not hydrogen if n=3. The substituent X on the benzene nucleus is preferably a hydrogen or a meta or para substituent, selected from the group comprising halogen, typically chlorine atom, or some other non-released non-interfering species such as an alkyl group, conveniently up to C6 for example a methyl, ethyl or propyl group. Alternatively, X can represent a second amido-percarboxylic acid substituent of formula:

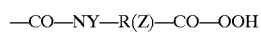

in which R, Y, Z and n are as defined above.

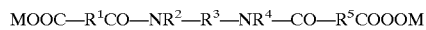

wherein $R^1$ is selected from the group consisting of $C_1$–$C_{12}$ alkylene, $C_5$–$C_{12}$ cycloalkylene, $C_6$–$C_{12}$ arylene and radical combinations thereof; R Hydrogen Peroxide Source Inorganic perhydrate salts are a preferred source of hydrogen peroxide.

Examples of inorganic perhydrate salts include perborate, percarbonate, perphosphate, persulfate and persilicate salts. The inorganic perhydrate salts are normally the alkali metal salts. The inorganic perhydrate salt may be included as the crystalline solid without additional protection. For certain perhydrate salts however, the preferred executions of such granular compositions utilize a coated form of the material which provides better storage stability for the perhydrate salt in the granular product. Suitable coatings comprise inorganic salts such as alkali metal silicate, carbonate or borate salts or mixtures thereof, or organic materials such as waxes, oils, or fatty soaps.

Sodium perborate is a preferred perhydrate salt and can be in the form of the monohydrate of nominal formula $NaBO_2H_2O_2$ or the tetrahydrate $NaBO_2H_2O_2.3H_2O$.

Alkali metal percarbonates, particularly sodium percarbonate are preferred perhydrates herein. Sodium percarbonate is an addition compound having a formula corresponding to $2Na_2CO_3.3H_2O_2$, and is available commercially as a crystalline solid.

Potassium peroxymonopersulfate is another inorganic perhydrate salt of use in the detergent compositions herein.

Hydrophilic Bleach

In the method herein or in the compositions herein, a hydrophilic bleaching agent may be present in addition to the hydrophobic bleaching agent. A suitable hydrophilic bleaching agent is TAED.

Preferably the hydrophilic bleaching agent is present at a ratio to the hydrophobic peroxyacid from 1:5 to 5:1, more preferably from 1:3 to 3:1, most preferably from 1:2 to 2:1

Detergent Compositions

The hydrophobic bleaching agent herein is preferably present in a detergent composition, when used to reduce the activity of micro-organisms.

Thus, the reduction of the activity preferably takes place during a cleaning method, preferably a automatic or hand laundry or dish washing method, in particularly at low temperatures up to 60° C. or even 45° C. or even 30° C.

When the hydrophobic peroxyacid bleaching agent contains a peroxyacid bleach precursor, the precursor is typically present at a level of from 0.05% to 20% by, more preferably from 0.5% to 10% by weight, most preferably from 1% to 7% by weight of the composition. When the hydrophobic peroxyacid bleaching agent contains a preformed hydrophobic peroxyacid, the preformed peroxyacid is typically present at a level of from 0.05% to 15% by weight, more preferably from 1% to 10% by weight of the composition.

The hydrogen peroxide sources, when present, are preferably incorporated in the compositions herein the form of the alkali metal, preferably sodium salt at a level of from 1% to 40% by weight, more preferably from 2% to 30% by weight and most preferably from 5% to 25% by weight of the compositions.

The hydrophilic bleach, when present, may preferably be present at a level of from 0.5% to 12% by weight of the composition.

The detergent compositions herein may comprise any additional ingredients, commonly employed in detergents. The precise nature of these additional components, and levels of incorporation thereof will depend on the physical form of the composition and the precise nature of the washing operation for which it is to be used.

The compositions preferably contain one or more additional detergent components selected from surfactants, effervescence sources, bleach catalysts, chelating agnets, bleach stabilisers, alkalinity systems, builders, phosphate-containing builders, organic polymeric compounds, enzymes, suds suppressors, lime soap, dispersants, soil suspension and anti-redeposition agents, soil releasing agents, perfumes, dyes, dyed speckles, brighteners, photobleaching agents and additional corrosion inhibitors.

Laundry Washing Method

Machine laundry methods herein typically comprise treating soiled laundry with an aqueous wash solution in a washing machine having dissolved or dispensed therein an effective amount of a machine laundry detergent composition containing the hydrophobic bleaching agent in accord with the invention. By an effective amount of the detergent composition it is meant from 10 g to 300 g of product dissolved or dispersed in a wash solution of volume from 5 to 65 litres, as are typical product dosages and wash solution volumes commonly employed in conventional machine laundry methods. Dosage is dependent upon the particular conditions such as water hardness and degree of soiling of the soiled laundry. The pH of the washing liquor is typically above 7, preferably above 8.5 or above 9 or even 9.5.

The detergent composition may be dispensed for example, from the drawer dispenser of a washing machine or may be sprinkled over the soiled laundry placed in the machine.

In one use aspect a dispensing device is employed in the washing method. Especially preferred dispensing devices for use with the composition of the invention have been described in the following patents; GB-B-2, 157, 717, GB-B-2, 157, 718, EP-A-0201376, EP-A-0288345 and EP-A-0288346. An article by J.Bland published in Manufacturing Chemist, November 1989, pages 41–46 also describes especially preferred dispensing devices for use with granular laundry products which are of a type commonly know as the "granulette". Another preferred dispensing device for use with the compositions of this invention is disclosed in PCT Patent Application No. WO94/11562.

Machine Dishwashing Method

Any suitable methods for machine dishwashing or cleaning soiled tableware.

A preferred machine dishwashing method comprises treating soiled articles selected from crockery, glassware, hollowware, silverware and cutlery and mixtures thereof, with an aqueous liquid having dissolved or dispensed therein an effective amount of a machine dishwashing composition herein. By an effective amount of the machine dishwashing composition it is meant from 8 g to 60 g of product dissolved or dispersed in a wash solution of volume from 3 to 10 litres, as are typical product dosages and wash solution volumes commonly employed in conventional machine dishwashing methods.

What is claimed is:

1. A method of reducing of the activity of micro-organisms containing a cell wall that contains high levels of peptidoglycan, said method comprising the steps of contacting said micro-organisms with an aqueous liquor having a pH greater than 8.5, said liquor comprising a hydrophobic bleaching agent comprising a peroxyacid having a carbon chain of at least 9 carbon atoms.

2. A method according to claim 1 wherein said peroxyacid having a carbon chain of at least 9 carbon atoms is present in said liquor at a level of at least 100 ppm per $10^6$ micro-organism.

3. A method according to claim 2, wherein said liquor comprises a detergent composition comprising a hydrophobic peroxyacid precursor, said hydrophobic peroxyacid precursor being present in said detergent composition at a level of at least 1% by weight of said detergent composition.

4. A method according to claim 2 wherein said micro-organisms are selected from the group consisting of yeast, gram positive bacteria and mixtures thereof.

5. A method according to claim 2, wherein said contacted micro-organisms are contacted with said liquor while said organisms are present on a fabric.

6. A method according to claim 2, wherein said contacted micro-organisms are contacted with said liquor while said organisms are present on a hard surface.

7. A method according to claim 3, wherein said hydrophobic peroxyacid precursor is present in said detergent composition at a level of from 1% by weight to 10% by weight of said detergent composition.

8. A method according to claim 7 wherein said micro-organisms are selected from the group consisting of yeast, gram positive bacteria and mixtures thereof.

9. A method according to claim 8, wherein said contacted micro-organisms are contacted with said liquor while said organisms are present on a fabric.

10. A method according to claim 8, wherein said contacted micro-organisms are contacted with said liquor while said organisms are present on a hard surface.

11. A method according to claim 2, wherein said liquor comprises a hydrogen peroxide source.

12. A method according to claim 2, wherein said peroxyacid comprises an N-acyl group.

13. A method according to claim 2, wherein said hydrophobic bleaching agent comprises a 6-(nonanamidocaproyl) oxybenzene sulphonate salt.

14. A method of reducing of the activity of micro-organisms selected from the group consisting of yeast, gram positive bacteria, gram negative bacteria and mixtures thereof, comprising the steps of contacting said micro-organisms with an aqueous liquor having a pH greater than 8.5, said liquor comprising a hydrophobic bleaching agent comprising a peroxyacid having a carbon chain of at least 9 carbon atoms and a hydrophilic bleaching agent.

15. A method according to claim 14 wherein said peroxyacid having a carbon chain of at least 9 carbon atoms is present in said liquor at a level of at least 100 ppm per $10^6$ micro-organism.

16. A method according to claim 14, wherein said hydrophilic bleaching agent comprises TAED.

* * * * *